(12) United States Patent
Castillo (10) Patent No.: US 9,693,887 B2
(45) Date of Patent: Jul. 4, 2017

(54) MULTI-PIECE JOINT GUARD

(71) Applicant: ASTERISK, LLC, Corona, CA (US)

(72) Inventor: Daniel Castillo, Laguna Beach, CA (US)

(73) Assignee: Asterick, LLC, Corona, CA (US)

( * ) Notice: Subject to any disclaimer, the term of this patent is extended or adjusted under 35 U.S.C. 154(b) by 220 days.

(21) Appl. No.: 14/571,565

(22) Filed: Dec. 16, 2014

(65) Prior Publication Data

US 2015/0173927 A1 Jun. 25, 2015

Related U.S. Application Data

(63) Continuation of application No. 61/918,827, filed on Dec. 20, 2013.

(51) Int. Cl.
*A61F 5/01* (2006.01)

(52) U.S. Cl.
CPC .................................. *A61F 5/0123* (2013.01)

(58) Field of Classification Search
CPC .................. A61F 5/0123; A61F 5/0102; A61F 2005/0139
See application file for complete search history.

(56) References Cited

U.S. PATENT DOCUMENTS

| 4,884,561 A | 12/1989 | Letson, Sr. | |
| 7,608,051 B1* | 10/2009 | Nace | A61F 5/0123 602/1 |
| 2011/0098618 A1* | 4/2011 | Fleming | A61F 5/0123 602/16 |
| 2012/0157902 A1* | 6/2012 | Castillo | A61F 5/0123 602/26 |
| 2012/0240303 A1 | 9/2012 | Matta et al. | |

OTHER PUBLICATIONS

International Search Report and Written Opinion for International Application No. PCT/US2014/070953; Mar. 31, 2015; 10 pages.

* cited by examiner

*Primary Examiner* — Gary Jackson
*Assistant Examiner* — Scott T Luan
(74) *Attorney, Agent, or Firm* — Stetina Brunda Garred and Brucker (57) ABSTRACT

A protective patella guard adapted for use with a knee brace having upper and lower frame members. The protective patella guard including an upper cup element coupled to the upper frame member, a lower cup element coupled to the lower frame member, and an intermediate cup element operatively coupled to the upper cup element and lower cup element. The patella guard is transitional between a first configuration and a second configuration, wherein a degree of overlap between the upper cup element, the lower cup element, and the intermediate cup element decreases as the patella guard transitions from the first configuration to the second configuration.

3 Claims, 5 Drawing Sheets

MULTI-PIECE JOINT GUARD

CROSS-REFERENCE TO RELATED APPLICATIONS

This application claims the benefit of U.S. Provisional Application No. 61/918,827, filed Dec. 20, 2013, the contents of which are expressly incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates generally to protective orthopedic equipment, and more specifically, to an expandable patella guard adapted to provide substantially continuous coverage over the wearer's patella as a corresponding brace is transitioned between an extended configuration and a flexed configuration.

2. Description of the Related Art

Protective orthopedic equipment, such as knee braces are well known in the art and are designed to protect a wearer's knee joint from injury, particularly during physical activities, such as motorcycle racing, skiing, football, basketball, and the like. In general, knee braces limit the range of motion of the knee joint to a safe range of motion, e.g., knee braces restrict the joint from movement which may otherwise cause ligament tears, meniscus tears, hyperextension, or other injuries.

Conventional knee braces generally include an upper frame member, a lower frame member, and a pivot member pivotally connecting the upper frame member to a lower frame member. The upper and lower frame members are pivotable relative to the pivot member to define the pivotal range of motion of the knee joint. The knee brace is generally positionable on the wearer's leg about the knee, such that the upper frame member extends slightly above the wearer's knee along the wearer's thigh and the lower frame member extends slightly below the wearer's knee along the wearer's shin. Operation of the knee brace is typically most effective when the brace is properly positioned on the wearer's knee, which in most cases means that the wearer's knee and the brace pivot about substantially the same axis.

As indicated above, conventional knee braces are primarily directed toward limiting movement of the knee joint within a safe range of motion. Consequently, conventional knee braces are not largely concerned with providing coverage over the knee. As such, one area of the knee that oftentimes remains exposed by a knee joint is the patella, e.g., "kneecap." The patella is a bone which articulates with the femur and covers an articulating surface of the knee joint to provide protection thereto. When the patella experiences a direct blow, the patella may fracture.

In view of the susceptibility of patellar fractures, some knee braces include a patella cup which is loosely connected to the frame of the knee brace to provide a limited amount of coverage over the wearer's patella. Most patella cups are of single piece construction, and thus, may be connected to the brace frame via a tether which has enough slack to allow the brace to flex. As the brace flexes, the patella cup may move out of alignment with the wearer's patella, thereby making the patella vulnerable to injury. Therefore, while conventional braces may employ a patella cup, such traditional patella cups do not provide continuous coverage over the wearer's patella as the knee brace is flexed.

Accordingly, there is a need in the art for a patella guard which provides more continuous coverage of the wearer's patella as the corresponding knee brace is transitioned between an extended configuration and a flexed configuration. Various aspects of the present invention address this particular need, as will be discussed in more detail below.

BRIEF SUMMARY OF THE INVENTION

In accordance with one embodiment of the present invention, there is provided a protective patella guard specifically configured and adapted to provide substantially continuous coverage over a user's patella while a corresponding knee brace is selectively transitioned between a flexed configuration and an extended configuration. The patella guard is a multi-piece device having an upper element which follows the motion of the user's upper leg, a lower element which follows the motion of the user's lower leg, and an intermediate or center element coupled to the upper and lower elements and moveable relative thereto such that the motion of the center element is timed relative to the upper and lower elements so as to prevent a gap from forming throughout the range of motion of the brace.

According to one embodiment, the patella guard is suitable for use with an orthopedic brace having an upper frame member and a lower frame member pivotally coupled to the upper frame member. The protective patella guard includes an upper cup element configured to be connectable to the upper frame member, a lower cup element configured to be connectable to the lower frame member, and an intermediate cup element operatively coupled to the upper cup element and lower cup element. The patella guard is transitional between a first configuration and a second configuration, wherein a degree of overlap between the upper cup element, the lower cup element, and the intermediate cup element decreases as the patella guard transitions from the first configuration to the second configuration.

The upper cup element, lower cup element, and intermediate cup element may be configured such that movement of the cup elements relative to each other is coordinated to maintain coverage over a wearer's patella as the patella guard transitions between the first configuration and the second configuration.

The intermediate cup element may maintain a minimal degree of overlap with at least one of the upper cup element and the lower cup element as the patella guard transitions between the first configuration and the second configuration.

The patella guard may additionally include a first driving arm coupled to the intermediate cup element and a second driving arm coupled to one of the upper cup element and the lower cup element. The first and second driving arms may include cooperatively engageable gear elements. The cooperatively engageable gear elements may be sized and configured to effectuate counter-rotation of the first driving arm relative to the second driving arm.

The intermediate cup element may define a concave inner surface and an opposing convex outer surface. The convex outer surface may be located between the concave inner surface and the upper cup element when the patella guard is in the first configuration. The convex outer surface may be located between the concave inner surface and the lower cup element when the patella guard is in the first configuration.

One of the upper cup element and the lower cup element may be positionable between the other one of the upper cup element and the lower cup element and the intermediate cup element when the patella guard is in the first configuration.

The patella guard may include a lip formed on the upper cup element. The lip may be sized and configured to engage the lower cup element when the patella guard is in the first configuration to limit further movement of the lower cup element relative to the upper cup element.

According to another embodiment, there is provided a knee brace comprising an upper frame member and a lower frame member pivotally coupled to the upper frame member. The knee brace also includes the protective patella guard.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION OF THE INVENTION

The detailed description set forth below in connection with the appended drawings is intended as a description of certain embodiments of an articulating, multi-piece patella guard and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating a preferred embodiment of the present invention, and not for purposes of limiting the same, there is depicted a knee brace 10 including a multi-piece, articulating patella guard 12. The patella guard 12 is specifically configured and adapted to provide substantially continuous coverage of the wearer's patella while the knee brace 10 articulates with the wearer's knee. In this respect, when the patella guard 12 is integrated into the knee brace 10, the brace 10 provides enhanced protection of the wearer's patella relative to conventional knee braces.

According to one embodiment, the knee brace 10 includes an upper frame member 14 adapted to be connectable to a first limb structure of the wearer, e.g., the upper leg, and a lower frame member 16 adapted to be connectable to a second limb structure of the wearer, e.g., the lower leg. The upper frame member 14 includes an upper medial element 18 (see FIG. 2) and an upper lateral element 20 (see FIG. 2) coupled to the upper medial element 18. The upper frame member 14 may be formed from a strong, durable material, such as a metal, a polymeric material, or other materials known in the art. An upper cuff 22 is coupled to the upper frame member 14 and is selectively adjustable to conform to the size of the wearer's leg. In particular, the upper cuff 22 may be circumferentially adjustable to tightly conform to the size of the wearer's upper leg. For more information regarding an adjustable upper cuff, please refer to United States Patent Application Publication No. 2008/0108922, entitled Joint Brace with Adjustable Limb Extension Regulator, the contents of which are expressly incorporated herein by reference.

The lower frame member 16 is configured similar to the upper frame member 14, and includes a lower medial element 24 (see FIG. 2) and a lower lateral element 26 (see FIG. 2) coupled to the lower medial element 24. The lower frame member 16 may be formed from a strong, durable material, such as metal, a polymer material, or other materials known in the art. A lower cuff 28 is coupled to the lower frame member 16 and is selectively adjustable to conform to the size of the wearer's lower leg. In particular, the lower cuff 28 may be circumferentially adjustable in a manner similar to the upper cuff 22 described above.

Figure 1:
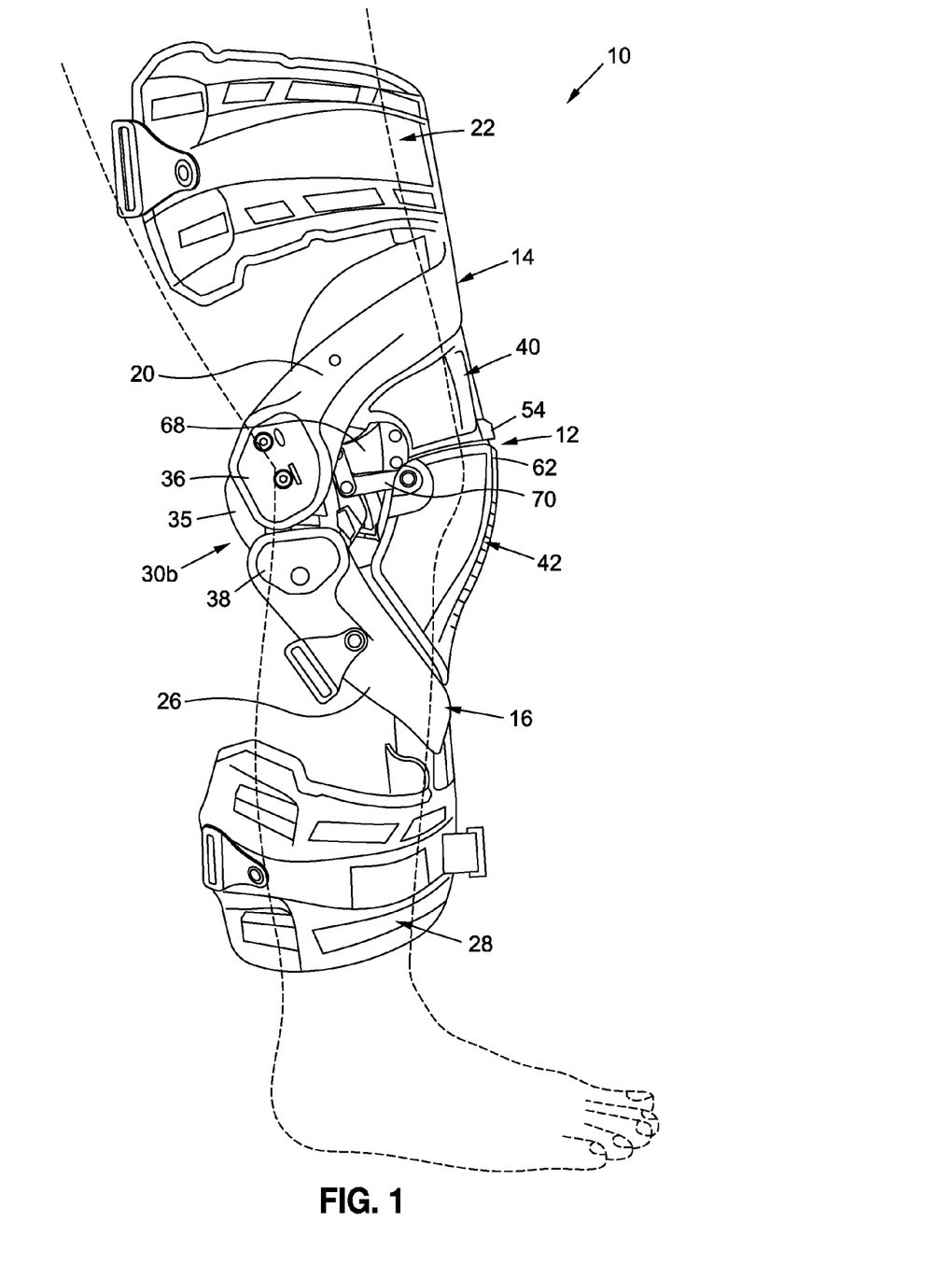
FIG. 1 is a first side view of a knee brace constructed in accordance with an aspect of the present invention and positioned on a wearer's leg (shown in phantom)
Figure 3:
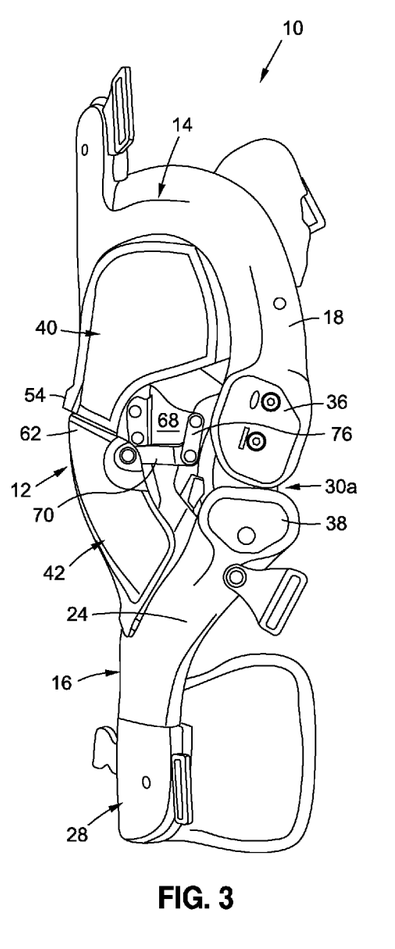
FIG. 3 is a second side view of the knee brace shown from the opposing side relative to the perspective depicted in FIG. 1.

The upper frame member 14 is pivotally coupled to the lower frame member 16 to allow the knee brace 10 to articulate with the wearer's knee. Along these lines, the knee brace 10 includes a pair of pivoting assemblies 30 located on opposed sides of the brace 10. A medial pivoting assembly pivotally 30a (see FIG. 3) couples the upper medial element 18 to the lower medial element 24. A lateral pivoting assembly 30b (see FIG. 1) pivotally couples the upper lateral element 20 to the lower lateral element 26.

Figure 4:
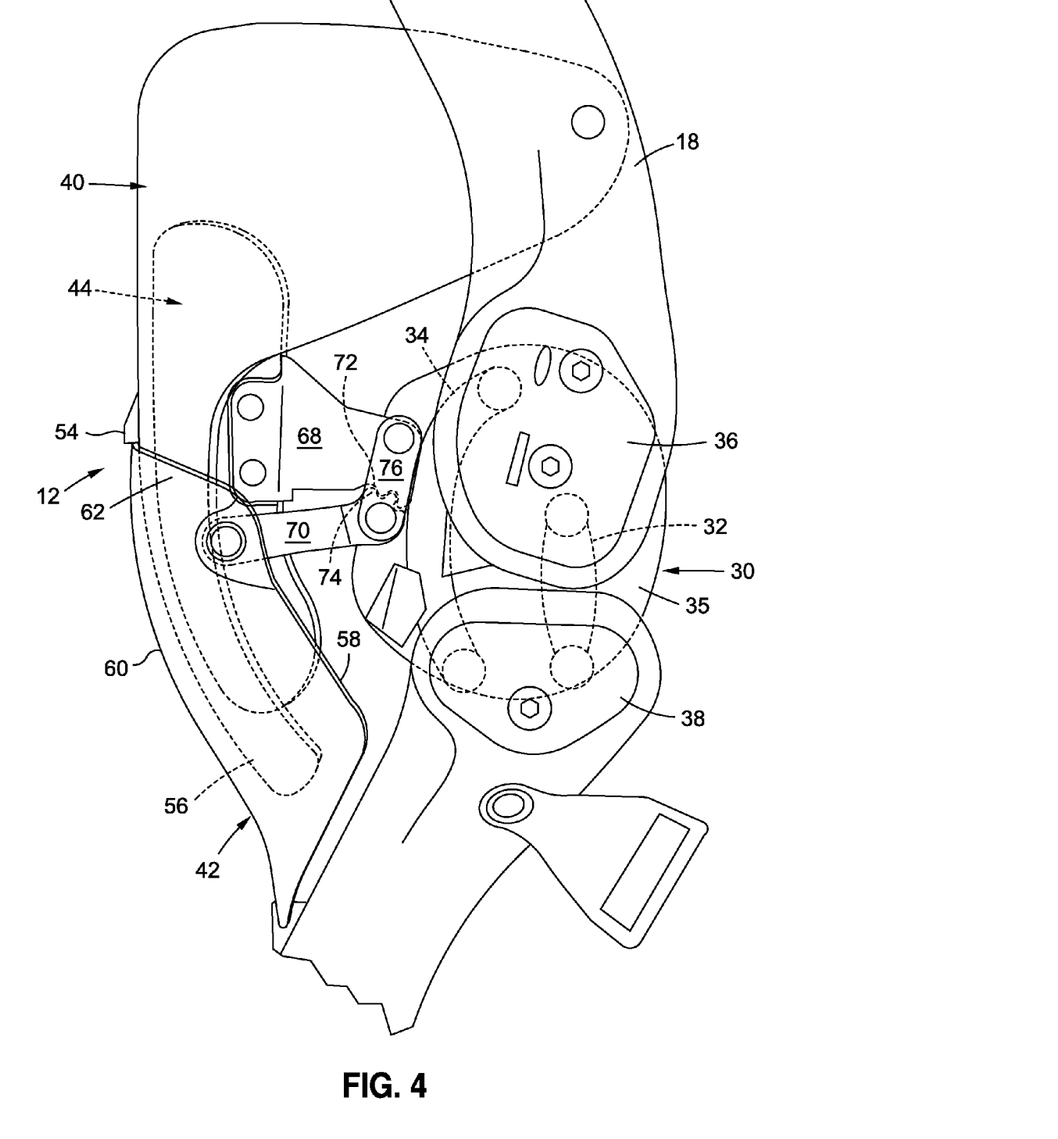
FIG. 4 is an enlarged side view of a pivoting section of the knee brace.

Referring now specifically to FIG. 4, each pivoting assembly 30 includes a first pivot arm 32, a second pivot arm 34, a condyle 35, a first pivot base 36 and a second pivot base 38. The first pivot arm 32 includes a first end portion pivotally coupled to the first pivot base 36 and a second end portion pivotally coupled to the second pivot base 38. Likewise, the second pivot arm 34 includes a first end portion pivotally coupled to the first pivot base 36 and a second end portion pivotally coupled to the second pivot base 38. Each pivot base 36, 38 may include a pair of sockets adapted to pivotally engage with the respective end portions of the first and second pivot arms 34, 36. The condyle 35 resides between the wearer's knee and the remaining portion of the pivoting assembly 30. The pivoting assemblies 30 are specifically configured and adapted to allow the upper and lower frame members 14, 16 to pivot relative to each other in a motion that substantially conforms with the pivoting motion of a human knee joint. For more information related to the pivoting assemblies, please refer to again to United States Patent Application Publication No. 2008/0108922, mentioned above.

The pivoting assemblies 30 enable the upper frame member 14 to pivot relative to the lower frame member 16 within a prescribed pivotal range of motion between a flexed configuration and an extended configuration. The internal angle (e.g., concave) between the upper frame member 14 and the lower frame member 16 increases as the knee brace 10 transitions from the flexed configuration toward the extended configuration. In other words, when the knee brace 10 is being worn by the wearer, and the wearer's leg is generally straight, the brace 10 assumes the extended configuration. However, when the wearer's leg is bent, the knee brace 10 assumes a flexed configuration.

The knee brace 10 additionally includes a protective patella guard 12 coupled to the upper frame member 14 and the lower frame member 16. The patella guard 12 is adapted to provide coverage over the wearer's patella as the brace 10 articulates between the flexed and extended configurations. According to one embodiment, the patella guard 12 includes an upper cup element 40 coupled to the upper frame member 14, a lower cup element 42 coupled to the lower frame member 16, and an intermediate cup element 44 (see FIGS. 4-6) operatively coupled to the upper cup element 40 and the lower cup element 42. The intermediate cup element 44 is adapted to remain positioned substantially over the knee cap as the knee brace 10 transitions between the extended configuration and the flexed configuration.

The upper cup element 40 includes an inner surface 46 (see FIG. 5) and an opposing outer surface 48. The inner surface 46 includes a portion that defines a generally concave configuration, while the outer surface 48 defines a generally convex configuration. According to one embodiment, the outer surface 48 includes an upper region 50 and a lower region 52 separated by a raised lip 54 which extends across the upper cup element 40 in a generally medial-lateral direction. The purpose of the lip 54 will be described in more detail below. The upper cup element 40 defines an upper end portion and an opposing upper cup distal end portion 56 extending away from the upper frame member 14. The upper end portion is coupled to the upper frame member 14 via a mechanical fastener, such as a rivet, screw, nail, adhesive, or other mechanical fasteners known in the art.

The lower cup element 42 includes an inner surface 58 (see FIG. 4) and an opposing outer surface 60. The inner surface 58 defines a generally concave configuration, while the outer surface 60 defines a generally convex configuration. The lower cup element 42 defines a lower end portion and an opposing lower cup distal end portion 62 extending away from the lower frame member 16. The lower end portion is coupled to the lower frame member 16 via a mechanical fastener.

The intermediate cup element 44 includes an inner surface 64 (see FIGS. 5-6) and an opposing outer surface 66, wherein the inner surface 64 defines a generally concave configuration and the outer surface 66 defines a generally convex configuration. The intermediate cup element 44 is configured such that when the knee brace 10 is worn by the wearer, the inner surface 64 of the intermediate cup element 44 faces toward the wearer's knee, while the outer surface 66 faces away from the wearer's knee.

One unique aspect of the present invention relates to the position and movement of the patella guard 12 (e.g., the upper cup element 40, the intermediate cup element 44, and the lower cup element 42) when the knee brace 10 transitions between the extended configuration and the flexed configuration. In particular, the patella guard 12 is adapted to expand as the knee brace 10 transitions from the extended configuration toward the flexed configuration in order to maintain coverage over the wearer's knee cap. In this respect, while the knee brace 10 transitions between extended and flexed configurations, the patella guard 12 also transitions between a first, collapsed configuration corresponding to the knee brace extended configuration, and a second, expanded configuration corresponding to the knee brace flexed configuration.

Figure 2:
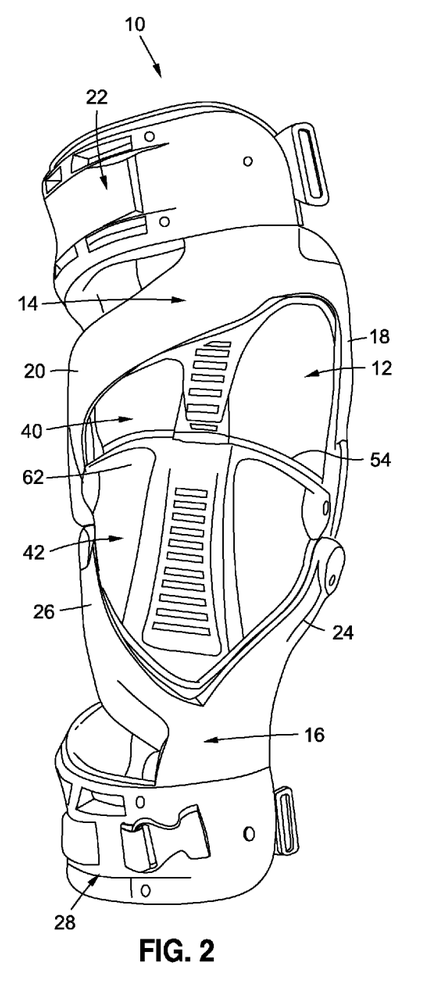
FIG. 2 is a front view of the knee brace depicted in FIG. 1.

The knee brace 10 shown in FIGS. 1-4 is in the extended configuration, and thus, the patella guard 12 is in the first configuration. When the patella guard 12 is in the first configuration, the intermediate cup element 44 is covered by the upper cup element 40 and the lower cup element 42. In other words, when the patella guard 12 is in the first configuration, the intermediate cup element 44 is generally hidden from view from a front perspective, as is shown in FIG. 2. In this respect, the upper cup element 40 and lower cup element 42 define a substantially continuous surface or shield extending between the upper frame member 14 and the lower frame member 16. In the exemplary embodiment, the distal end 62 of the lower cup element 42 overlaps the distal end 56 of the upper cup element 40 to cover the intermediate element 44 when the patella guard 12 is in the first configuration. More specifically, the distal end 62 of the lower cup element 42 is disposed adjacent the lip 54 of the upper cup element 44. In most cases, the distal end 62 of the lower cup element 42 will be abutting the lip 54 of the upper cup element 44 when the patella guard 12 is in the first configuration. As such, a pad or resilient material may be coupled to the lip 54 to provide a "cushioned" stop when the knee brace 10 moves from the flexed configuration to the extended configuration.

Figure 7:
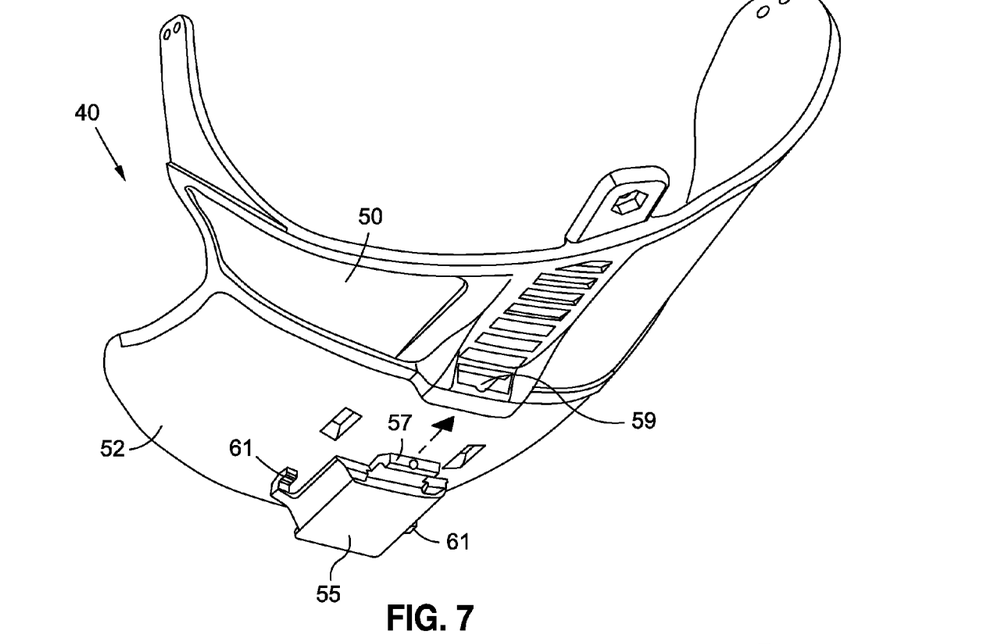
FIG. 7 is an exploded perspective view of an extension stop disengaged from an upper cup element.
Figure 8:
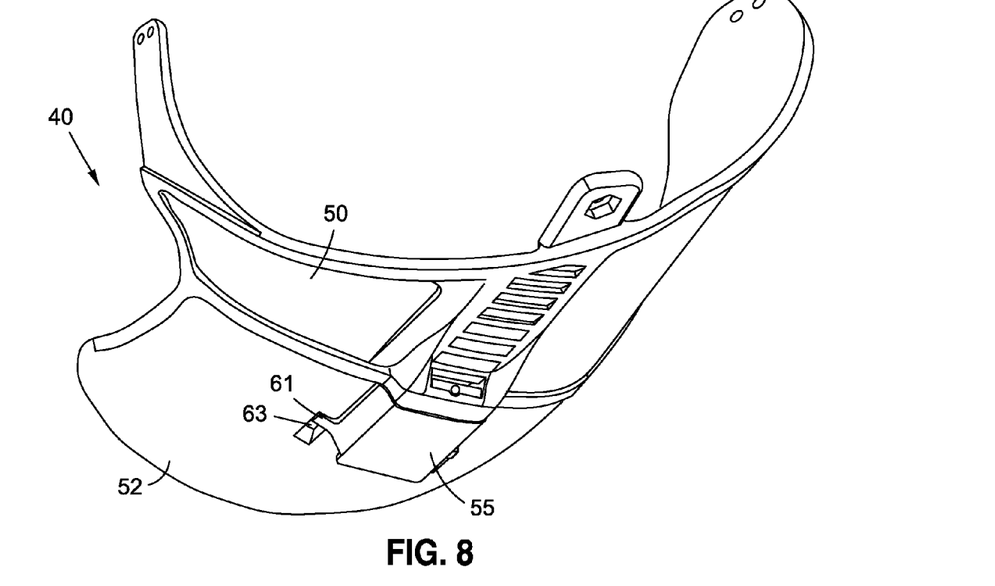
FIG. 8 is perspective view of the extension stop engaged with the upper cup element.

Referring now to FIGS. 7 and 8, other embodiments of the knee brace 10 may employ a stop member 55 in place of the lip 54 described above, to stop movement of the lower cup element 42 relative to the upper cup element 40 when the knee brace 10 transitions from the flexed configuration to the extended configuration. The stop element 55 may be snap engageable to the upper cup element 40. In particular, the stop element 55 may include a tab 57 that is inserted into a corresponding aperture 59. Furthermore, the stop element 55 may include a pair of engagement arms 61 that extend into respective ones of a pair of openings 63 formed on the upper cup element 40. The stop element 55 may also include a padded surface to provide a cushioned stop when the knee brace 10 is moved into the extended configuration.

In the exemplary embodiment, the patella guard 12 defines a layered or stacked configuration when the patella guard 12 is in the first configuration. The intermediate cup element 44 is at the innermost portion of the stack (e.g., that portion of the stack closest to the wearer). The lower region 52 of the upper cup element 40 is the middle portion of the stack, and the lower cup element 42 is the outer portion of the stack (e.g., that portion of the stack furthest from the wearer). In this respect, a portion of the upper cup element 40 is captured between the intermediate cup element 44 and the lower cup element 42 when the patella guard 12 is in the first configuration. Although the exemplary embodiment includes the upper cup element 40 residing between the intermediate cup element 44 and the lower cup element 42 when the patella guard 12 is in the first configuration, it is understood that in other embodiments, the lower cup element 42 may reside between the intermediate cup element 44 and the upper cup element 40. In such an embodiment, it may be desirable to form the lip 54 on the lower cup element 42 to provide a limiting stop member for the upper cup element 40. It is desirable to position the intermediate cup element 44 adjacent the wearer to prevent pinching when the upper and lower cup elements 40, 42 come together as the patella guard 12 approaches the first configuration.

Figures 5, 6:
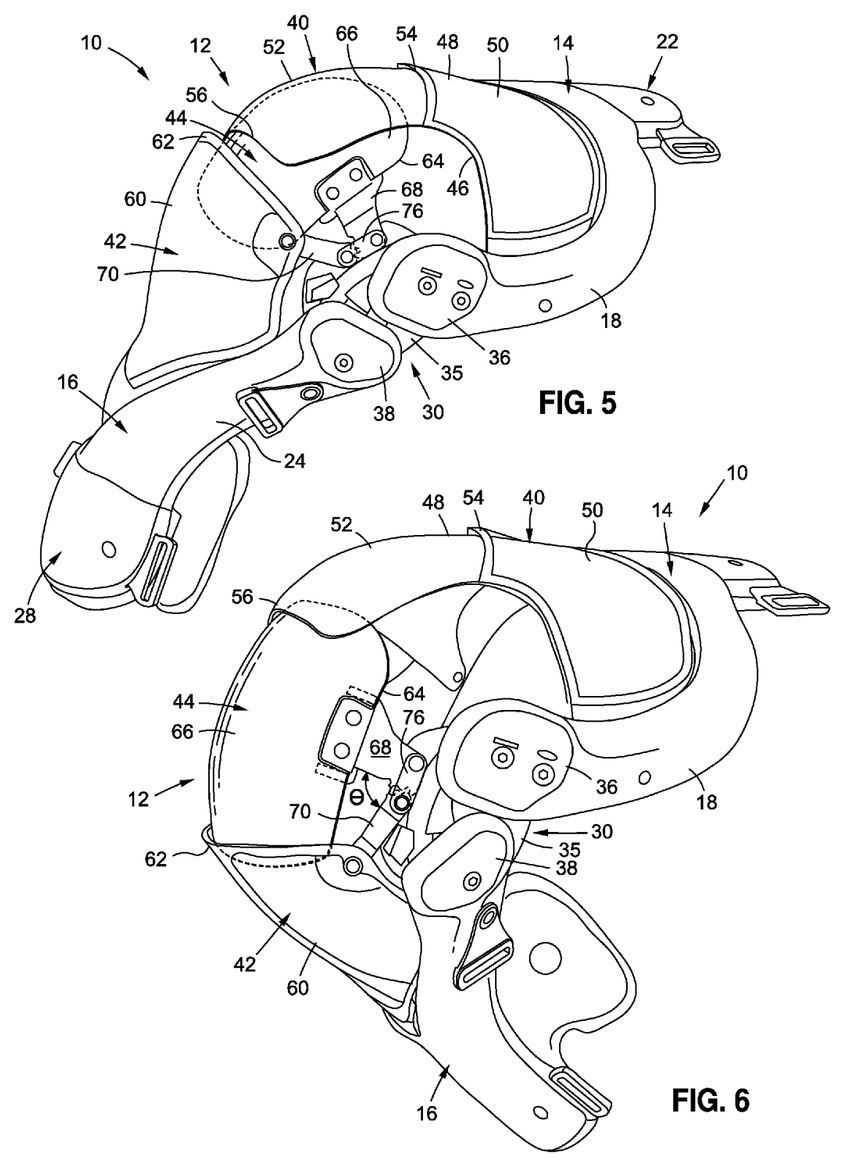
FIG. 5 is a perspective view of the knee brace in a partially flexed configuration.
FIG. 6 is a perspective view of the knee brace is a completely flexed configuration.

Referring now to FIGS. 5 and 6, the knee brace 10 is shown in different stages of transition from the extended configuration toward the flexed configuration. As the knee brace 10 transitions from the extended configuration toward the flexed configuration, the patella guard 12 also transitions from the first configuration (associated with the extended configuration) to the second configuration (associated with the flexed configuration). In particular, FIG. 5 shows the knee brace 10 in a partially flexed configuration, while FIG. 6 shows the knee brace 10 in a completely flexed configuration.

As the knee brace 10 transitions from the extended configuration toward the flexed configuration, the upper cup member 40 and lower cup member 42 begin to separate, which results in the exposure of the intermediate cup element 44. As such, the degree of overlap between the upper cup element 40, the lower cup element 42, and the intermediate cup element 44 decreases as the patella guard 12 transitions from the first configuration to the second configuration. In particular, the lower region 52 of the upper cup element 40 is withdrawn from being captured between the lower cup element 42 and the intermediate cup element 44, and the intermediate cup element 44 becomes exposed. When the knee brace 10 reaches the flexed configuration, the distal end 62 of the lower cup element 42 is disposed adjacent a lower end of the intermediate cup element 44, while the distal end 56 of the upper cup element 40 is disposed adjacent an upper end of the intermediate cup element 44. In this respect, when the patella guard 12 is in the second configuration, the upper and lower cup elements 40, 42 are located on substantially opposite ends of the intermediate cup element 44.

Although the foregoing describes the transition of the patella guard 12 between the first and second configuration in terms of the degree of overlap between the upper cup element 40, lower cup element 42, and intermediate cup element 44, such transition can also be described in terms of degree of exposure of the upper cup element 40 and/or the intermediate cup element 44. As to the upper cup element 40, when the patella guard 12 is in the first configuration, only a portion of the upper cup element 40 is exposed, namely, the upper region 50. As the patella guard 12 transitions from the first configuration toward the second configuration, the degree of exposure of the upper cup element 40 increases, such that when the upper cup element 40 reaches the second configuration, the entirety of the upper cup element 40 is exposed. Similarly, the degree of exposure of the intermediate cup element 44 increases as the patella guard 12 transitions from the first configuration toward the second configuration. In particular, when the patella guard 12 is in the first configuration, the entirety of the intermediate cup element 44 (or at least most of the intermediate cup element 44) is covered by the upper and lower cup elements 40, 42. As the patella guard 12 transitions from the first configuration toward the second configuration, the degree to which the intermediate cup element 44 is exposed increases, such that when the patella guard 12 is in the second configuration, most of the intermediate cup element 44 is exposed.

As knee brace 10 returns from the flexed configuration to the extended configuration, the patella guard 12 is adapted to transition from the second configuration to the first configuration. In this respect, the patella guard 12 transitions from the configuration shown in FIG. 6 to the configuration shown in FIGS. 1-4. As the patella guard 12 is moved from the second configuration toward the first configuration, both the upper and lower cup elements 40, 42 move toward each other and begin to cover the intermediate cup element 44. As such, the degree of exposure of the intermediate cup element 44 begins to decrease. Eventually, the lower region 52 of the upper cup element 40 is moved between the intermediate cup element 44 and the lower cup element 42, and thus, the degree of exposure of the upper cup element 40 begins to decrease. However, as the patella guard 12 continues from the second configuration toward the first configuration, the degree of overlap between the upper cup element 40, lower cup element 42, and intermediate cup element 44 increases. The patella guard 12 continues the transition from the second configuration toward the first configuration until the distal end 62 of the lower cup element 42 abuts the lip 54 formed on the upper cup element 40.

The unique, multi-piece configuration of the patella guard 12 allows the intermediate cup 44 to remain in place over the wearer's knee cap, despite flexion of the knee brace 10. Thus, the patella guard 12 protects the knee cap from experiencing a direct blow during a sports activity, which may otherwise result in a fracture or other injury to the knee cap.

As described above, the upper cup element 40, lower cup element 42 and intermediate cup element 44 are capable of moving independent of one another as the patella guard 12 transitions between the first and second configuration. One aspect of the invention is directed toward timing the movement of the cup elements 40, 42, 44 relative to each other. Along these lines, one embodiment of the invention includes a first driving arm 68 coupled to the intermediate cup element 44 and a second driving arm 70 coupled to the lower cup element 42. The first and second driving arms 68, 70 define an angle "$\theta$" therebetween (see FIG. 6). The first and second driving arms 68, 70 have cooperatively engageable gear elements 72, 74 (see FIG. 4) and are pivotally coupled to a common linking arm 76 and condyle 35. The cooperatively engageable gear elements 72, 74 are sized and configured to effectuate counter-rotation of the first driving arm 68 relative to the second driving arm 70 in a precisely timed manner corresponding to the geared engagement.

When knee brace 10 is in the extended configuration with the patella guard 12 in the first configuration (see FIG. 4), the angle $\theta$ between the first and second driving arms 68, 70 is at a minimum. As the knee brace 10 transitions from the extended configuration toward the flexed configuration, the movement of the lower frame member 16 causes the lower cup element 42 to move, which in turn moves the second driving arm 70. In particular, from the perspective shown in FIG. 4, the second driving arm 70 is pivoted in a counter-clockwise direction relative to the condyle 35. The counterclockwise rotation of the second driving arm 70 causes clockwise rotation of the first driving arm 68, which in turn causes movement of the intermediate cup element 44. In this respect, the movement of the intermediate cup element 44 relative to the lower cup element 42 is governed by the engagement between the gear elements 72, 74. The counterclockwise movement of the second driving arm 70 and the clockwise movement of the first driving arm 68 causes the angle $\theta$ to increase.

When the knee brace 10 is returned to the extended configuration from the flexed configuration, the movement of the lower frame member 16 and the attached lower cup element 42 causes the second driving arm 70 to move in a clockwise direction (from the perspective depicted in FIG. 4) relative to the condyle 35. The clockwise rotation of the second driving arm 790 causes counterclockwise rotation of the first driving arm 68, which in turn causes movement of the intermediate cup element 44 and the angle θ to decrease.

The timing of the movement between the lower cup element 42 and the intermediate cup element 44 can be changed by adjusting the length of the driving arms 68, 70 and/or the teeth on the gear elements 72, 74.

Although the foregoing describes an embodiment of present invention as a patella guard 12 integrated into a knee brace 10, it is understood that the patella guard 12 may be sold separately from the knee brace 10 and adapted to be subsequently attached to the brace 10. Furthermore, although the exemplary embodiment includes a patella guard 12, it is contemplated that a multi-piece joint guard can be incorporated into other joint braces/orthopedic braces, such as a shoulder brace having a multi-piece protective guard which covers the elbow joint.

It is also contemplated that the patella guard 12 may be adapted for use without a conventional brace. For instance, the upper cup element 40 may be adapted to be attachable to the wearer's thigh via a thigh attachment cuff, VELCRO™ strap, or the like, while the lower cup element 42 may be adapted to be attachable to the wearer's shin via a shin attachment cuff, VELCRO™ strap, or the like. The upper cup element 40 will track the motion of the wearer's thigh, while the lower cup element 42 will track the motion of the wearer's shin. The intermediate cup element 44 is configured to move relative to the upper cup element 40 and lower cup element 42 such that the wearer's patella remains covered as the patella guard 12 transitions between flexed and extended configurations.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A protective patella guard adapted for use by a wearer having a pivoting joint disposed between an upper limb and a lower limb, the protective patella guard comprising:
   an upper cup element configured to be connectable to the upper limb;
   a lower cup element configured to be connectable to the lower limb; and
   an intermediate cup element operatively coupled to the upper cup element and lower cup element;
   the patella guard being transitional between a first configuration and a second configuration, wherein a degree of overlap between the upper cup element, the lower cup element, and the intermediate cup element decreases as the patella guard transitions from the first configuration to the second configuration; and
   wherein one of the upper cup element and the lower cup element is positionable between the other one of the upper cup element and the lower cup element and the intermediate cup element when the patella guard is in the first configuration.

2. The knee brace recited in claim 1, wherein the upper cup element is positioned between the lower cup element and the intermediate cup element when the patella guard is in the first configuration.

3. An orthopedic brace comprising:
   an upper frame member and a lower frame member pivotally coupled to the upper frame member; and
   a protective guard including:
      an upper cup element coupled to the upper frame member;
      a lower cup element coupled to the lower frame member; and
      an intermediate cup element operatively coupled to the upper cup element and lower cup element;
   the protective guard being transitional between a first configuration and a second configuration, wherein a degree of overlap between the upper cup element, the lower cup element, and the intermediate cup element decreases as the protective guard transitions from the first configuration to the second configuration; and
   wherein one of the upper cup element and the lower cup element is positionable between the other one of the upper cup element and the lower cup element and the intermediate cup element when the protective guard is in the first configuration.

* * * * *